US00PP16098P2

(12) United States Plant Patent
Wood

(10) Patent No.: US PP16,098 P2
(45) Date of Patent: Nov. 8, 2005

(54) ***DEUTZIA* PLANT NAMED 'DUNCAN'**

(50) Latin Name: *Deutzia gracilis*
Varietal Denomination: Duncan

(75) Inventor: Timothy D. Wood, Grand Haven, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 60 days.

(21) Appl. No.: 10/878,428

(22) Filed: Jun. 28, 2004

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A new and distinct cultivar of *Deutzia* plant named 'Duncan', characterized by its compact plant habit; freely branching growth habit; bright yellow green-colored leaves; and numerous white-colored flowers.

1 Drawing Sheet

Botanical classification/cultivar designation: *Deutzia gracilis* cultivar Duncan.

BACKGROUND OF THE INVENTION

The present Invention relates to a new and distinct cultivar of *Deutzia* plant, botanically known as *Deutzia gracilis*, and hereinafter referred to by the name 'Duncan'.

The new *Deutzia* is a naturally-occurring branch mutation of a unidentified selection of *Deutzia gracilis*, not patented. The new *Deutzia* was discovered and selected by the Inventor as a branch of a plant within a population of plants of the parent selection in Grand Haven, Mich. in July, 2002.

Asexual reproduction of the new cultivar by softwood cuttings taken at Grand Haven, Mich. since July, 2002, has shown that the unique features of this new *Deutzia* are stable and reproduced true to type in successive generations of asexual reproduction.

SUMMARY OF THE INVENTION

The following traits have been repeatedly observed and are determined to be the unique characteristics of 'Duncan'. These characteristics in combination distinguish 'Duncan' as a new and distinct cultivar:

1. Compact plant habit.
2. Freely branching growth habit.
3. Bright yellow green-colored leaves.
4. Numerous white-colored flowers.

Plants of the new *Deutzia* are most similar to plants of the parent selection. In side-by-side comparisons conducted in Grand Haven, Mich., plants of the new *Deutzia* differed from plants of the parent selection in leaf color as plants of the parent selection had green-colored leaves. In addition, plants of the new *Deutzia* are more compact than plants of the parent selection.

BRIEF DESCRIPTION OF THE PHOTOGRAPH

The accompanying colored photograph illustrates the overall appearance of the new cultivar, showing the colors as true as it is reasonably possible to obtain in colored reproductions of this type.

The photograph is a close-up view of typical flowers and leaves of 'Duncan'. Flower and foliage colors in the photograph may differ slightly from the color values cited in the detailed botanical description which accurately describe the colors of the new *Deutzia*.

DETAILED BOTANICAL DESCRIPTION

The cultivar Duncan has not been observed under all possible environmental conditions. The phenotype may vary somewhat with variations in environment such as temperature and light intensity, without, however, any variance in genotype. The aforementioned photograph and following observations and measurements describe plants grown in Grand Haven, Mich., under commercial practice in an outdoor nursery during the spring and summer. During the production of the plants, day temperatures were about 21° C. and night temperatures were about 17° C. Plants used for the photograph and description were about one year old. In the following description, color references are made to The Royal Horticultural Society Colour Chart, 1995 Edition, except where general terms of ordinary dictionary significance are used.

Botanical classification: *Deutzia gracilis* cultivar Duncan.
Parentage: Naturally-occurring branch mutation of a unidentified selection of *Deutzia gracilis*, not patented.
Propagation:
- *Type cutting.*—Softwood cuttings.
- *Time to initiate roots.*—About ten days at 30° C.
- *Time to develop roots.*—About two months at 10° C.
- *Root description.*—Fibrous and freely branching.

Plant description:
- *General appearance.*—Deciduous shrub. Compact and outwardly arching plant habit; plants roughly rounded in shape.
- *Growth and branching habit.*—Freely branching; about 36 lateral brances develop per plant. Pinching, that is, removal of the terminal apices, enhances branching potential. Moderately vigorous.
- *Plant height.*—About 24 cm.
- *Plant diameter or spread.*—About 20 cm.

*Lateral branch description.*—Length: About 19 cm. Diameter: About 3.5 mm. Internode length: About 3 cm. Texture: Smooth, glabrous. Color: 141C.

*Foliage description.*—Arrangement: Opposite, simple. Length: About 6 cm. Width: About 1.5 cm. Shape: Lanceolate. Apex: Acuminate. Base: Attenuate. Margin: Slightly serrate. Texture, upper and lower surfaces: Smooth, glabrous. Venation pattern: Pinnate. Color: Developing and fully expanded foliage, upper surface: 151D; venation, same as lamina. Developing and fully expanded foliage, lower surface: 151D; venation, same as lamina. Petiole: Length: About 8 mm. Diameter: About 3 mm. Texture, upper and lower surfaces: Smooth, glabrous. Color, upper and lower surfaces: 144C.

Flower description:

*Flower type and habit.*—Single star-shaped flowers arranged on terminal panicles. Very freely flowering with about 24 flowers per inflorescence and about 576 flowers and flower buds per lateral branch. Flowers last about three to four weeks on the plant. Flowers not persistent. Flowers slightly fragrant, sweet.

*Flowering season.*—In the garden, flowering is continuous during the month of May in Grand Haven, Mich.

*Flower diameter.*—About 1.8 mm.

*Flower depth.*—About 1 cm.

*Flower buds.*—Length: About 7 mm. Diameter: About 4 mm. Shape: Ovoid. Color: 155B.

*Petals.*—Quantity: Five per flower. Petal length: About 9 mm. Petal width: About 5 mm. Shape: Elliptic. Apex: Obtuse to acute. Base: Attenuate. Margin: Entire. Texture, upper and lower surfaces: Smooth, glabrous. Color: When opening, upper and lower surfaces: Lighter than 155D. Fully opened, upper and lower surfaces: Lighter than 155D.

*Sepals.*—Quantity: About six. Calyx length: About 4 mm. Calyx diameter: About 4 mm. Shape: Lanceolate. Apex: Acute. Margin: Entire. Texture, upper and lower surfaces: Smooth, glabrous. Color, upper and lower surfaces: 145C.

*Peduncles.*—Length: About 7 cm. Diameter: About 2 mm. Texture: Smooth, glabrous. Strength: Strong. Angle to stem: About 20° from vertical. Color: 143C.

*Pedicels.*—Length: About 4 mm. Diameter: About 1 mm. Texture: Smooth, glabrous. Angle to stem: About 40° from vertical. Color: 143C.

*Reproductive organs.*—Stamens: Quantity: Ten per flower. Anther shape: Round. Anther length: Less than 1 mm. Anther color: 12C. Pollen amount: Scarce. Pollen color: 12C. Pistils: Quantity: Five per flower. Pistil length: About 5 mm. Stigma color: 155D. Style length: About 5 mm. Style color: 155D. Ovary color: 146A. Seeds/fruits: Seed and fruit development has not been observed.

Disease/pest resistance: Plants of the new *Deutzia* have not been observed to be resistant to pathogens and pests common to *Deutzia*.

Temperature tolerance: Plants of the new *Deutzia* have been observed to tolerate temperatures from −30 to 35° C.

It is claimed:

1. A new and distinct cultivar of *Deutzia* plant named 'Duncan', as illustrated and described.

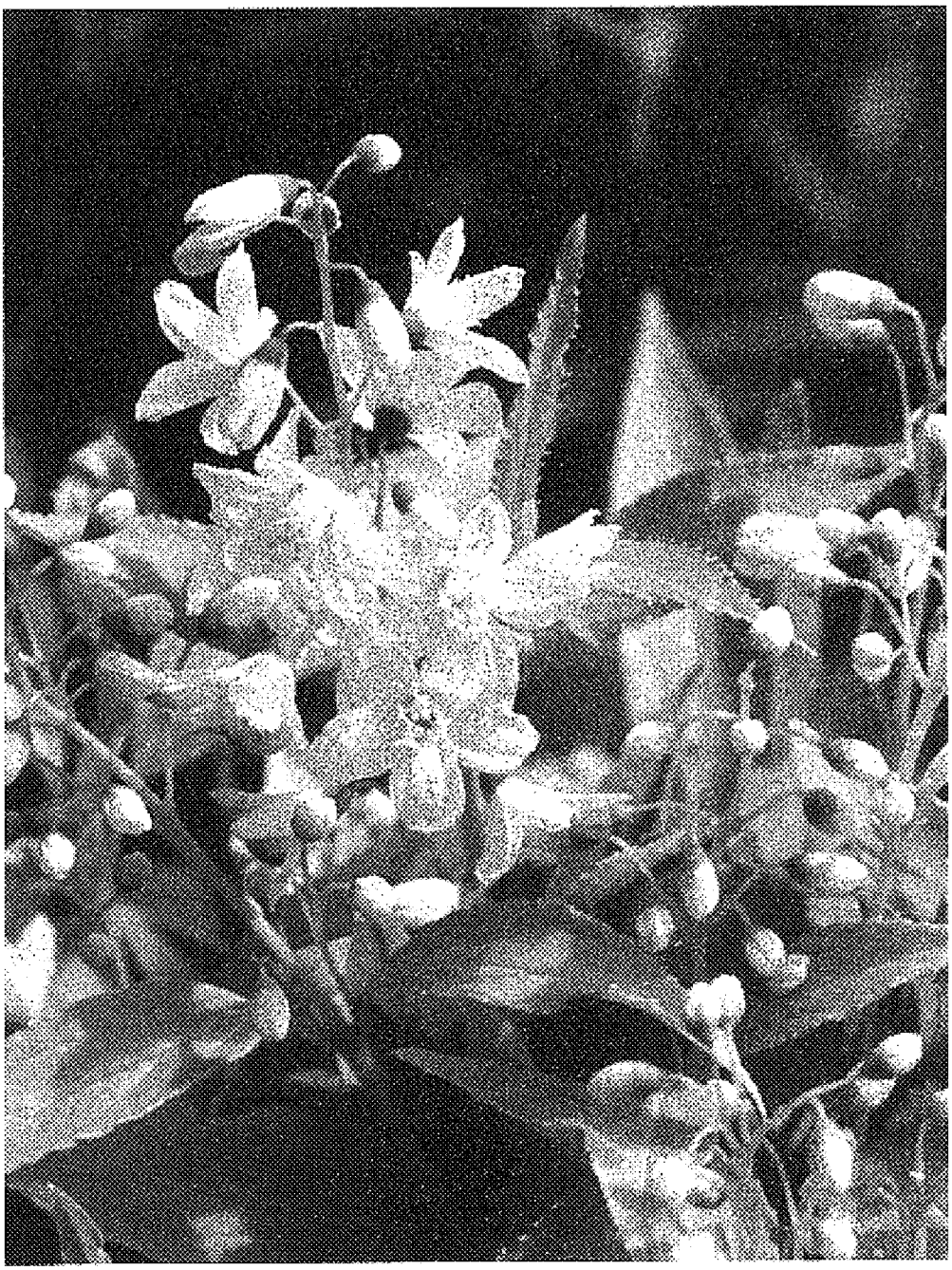

* * * * *